United States Patent [19]
Corbett, III et al.

[11] Patent Number: 5,630,839
[45] Date of Patent: May 20, 1997

[54] MULTI-ELECTRODE COCHLEAR IMPLANT AND METHOD OF MANUFACTURING THE SAME

[75] Inventors: Scott S. Corbett, III; John W. Swanson; Jerry Martyniuk, all of Portland, Oreg.; Thomas R. Clary, Issaquah, Wash.; Francis A. Spelman, Seattle, Wash.; Ben Clopton, Bainbridge Island, Wash.; Arne H. Voie; Claude N. Jolly, both of Seattle, Wash.

[73] Assignees: PI Medical Corporation, Portland, Oreg.; University of Washington, Seattle, Wash.; a part interest

[21] Appl. No.: 516,861

[22] Filed: Aug. 18, 1995

Related U.S. Application Data

[63] Continuation-in-part of Ser. No. 482,189, Jun. 7, 1995, Pat. No. 5,515,848, which is a continuation of Ser. No. 136,650, Oct. 14, 1993, abandoned, which is a continuation-in-part of Ser. No. 46,658, Apr. 12, 1993, abandoned, which is a division of Ser. No. 781,494, Oct. 22, 1991, Pat. No. 5,201,903.

[51] Int. Cl.$^6$ ..................................................... A61N 1/05
[52] U.S. Cl. ............................................................. 607/137
[58] Field of Search ............................. 607/56, 116, 136, 607/137

[56] References Cited

U.S. PATENT DOCUMENTS

| | | | |
|---|---|---|---|
| 4,261,372 | 4/1981 | Hansen et al. | 128/784 |
| 4,284,085 | 8/1981 | Hansen et al. | 128/784 |
| 4,648,403 | 3/1987 | Van Compernolle | 128/419 |
| 4,686,765 | 8/1987 | Byers et al. | 29/858 |
| 4,741,339 | 5/1988 | Harrison et al. | 128/419 |
| 4,762,135 | 8/1988 | van der Puije et al. | 128/784 |
| 4,809,712 | 3/1989 | Kuzma | 128/784 |
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 4,945,342 | 7/1990 | Steinemann | 607/116 |
| 4,961,434 | 10/1990 | Stypulkowski | 128/784 |
| 5,000,194 | 3/1991 | van den Honert et al. | 128/784 |
| 5,042,084 | 8/1991 | Daly | 455/41 |
| 5,178,957 | 1/1993 | Kolpe et al. | 428/458 |
| 5,232,549 | 8/1993 | Cathey et al. | 456/633 |
| 5,336,636 | 8/1994 | Burmer | 437/173 |

FOREIGN PATENT DOCUMENTS

| | | | |
|---|---|---|---|
| 0215726 | 3/1987 | European Pat. Off. | A61N 1/40 |
| WO 93/06698 | 4/1993 | WIPO | H04R 25/00 |
| 9400088 | 1/1994 | WIPO | A61F 11/04 |

OTHER PUBLICATIONS

Rubinstein, J.T., et al., "Current Density Profiles of Surface Mounted and Recessed Electrodes for Neural Prostheses," Reprinted from *IEEE Transactions on Biomedical Engineering*, vol. BME–34, No. 11 (Nov. 1987).

Mercer et al, "IEEE Transactions on Biomedical Engineering", vol. BME 25, No. 6, Nov. 1978, pp. 494–500.

Hochmair–Desoyer et al, "IEEE Transactions on Biomedical Engineering", vol. BME 27, No. 1, Jan. 1980, pp. 44–50.

*Primary Examiner*—William E. Kamm
*Attorney, Agent, or Firm*—Stoel Rives LLP

[57] ABSTRACT

A multi-electrode cochlear implant is taught in which approximately twenty or more insulated metal wires are wound around a flexible tube. These wires are held in place with a further layer of dielectric insulating material. The insulation is selectively removed with a laser beam to form electrodes. Two or more layers or valences of wires can be used, with the inner layer of wires terminating distal to the outer layers to provide a stepwise approximation of the tapering of the scala tympani. A core of shape memory material may be introduced into the tube, so that the implant will retain an effective shape after implantation.

27 Claims, 3 Drawing Sheets

MULTI-ELECTRODE COCHLEAR IMPLANT AND METHOD OF MANUFACTURING THE SAME

This invention was made with government support under grant 1 R41DC02424-01 awarded by the National Institutes of Health. The government has certain rights in the invention.

This application is a continuation-in-part of Corbett, III et al. U.S. patent application Ser. No. 08/482,189, filed Jun. 7, 1995, now U.S. Pat. No. 5,515,848 which is a file-wrapper-continuation of U.S. patent application Ser. No. 08/136,650, filed Oct. 14, 1993, now abandoned which is a continuation-in-part of U.S. patent application Ser. No. 08/046,658, filed Apr. 12, 1993, since abandoned, which is a division of U.S. patent application Ser. No. 07/781,494, filed Oct. 22, 1991, now U.S. Pat. No. 5,201,903.

BACKGROUND OF THE INVENTION

The present invention relates to a cochlear implant. More specifically it relates to a cochlear implant with an increased density and improved quality of electrodes and having physical characteristics which allow it to be placed into a more complete and more effective contact with the cochlea.

Most cases of profound hearing loss may be successfully addressed by a prosthesis that induces the electrical stimulation of the cochlea in response to sound received by a nearby microphone. (The cochlea is an organ of the inner ear, shaped like a snail, in which the auditory neurons have their receptive terminus.) Great efforts have been made over the last thirty years to address profound hearing loss in this manner.

The cochlea includes an electrolyte-solution-filled cavity shaped in the form of a tapering helix, known as the scala tympani. The receptive auditory neurons reside close to the interior or "Modiolar" wall of this cavity. These neurons may be stimulated by the application of electrical potential gradients to this wall.

The range and utility of the prosthetic hearing realized depends on the accuracy and precision with which potential gradients can be applied to this wall. The task of producing potential gradients that exist only within a small selected volume requires many small accurately placed electrodes that may be controlled to work in unison. For example, it may be desirable to control three neighboring electrodes in a cooperative manner as a "triad" to produce desirable potential gradients. The ideal surface area for each electrode is on the order of 1,000 square microns or greater.

In the past it has been typical, due to the unsolved problem of accurate placement of the implant, for each electrode to be in the form of a ring encompassing the implant's lateral circumference. At the current state of the art, these rings could be spaced apart longitudinally by a minimum of 750 μm. With this configuration, regardless of the orientation of the implant, a portion of each electrode faces the modiolar wall.

This configuration of electrodes, however, precludes any manipulation in the lateral dimension of the potential gradients. The potential gradients produced by the ring electrodes decrease monotonically with increasing lateral distance from the electrodes. In contrast, a high density array of electrodes spaced in a grid both laterally and longitudinally can produce precisely shaped lateral gradients with steep, non-monotonic slopes. The auditory neurons, arranged parallel to these lateral gradients, should respond more vigorously to such gradients than to the relatively shallow gradients producible by ring electrodes.

These electrodes must present as low a resistance as is possible to the emission of electrical current from their surfaces. Although the current to be applied is typically very small, current density is significant over the small electrode surface.

Furthermore, each electrode must be resistant to corrosion by the solution that it contacts.

A commonly used method for producing an electrode entails the removal of a small area of insulating dielectric material from a wire, creating an electrode in the form of an exposed wire surface. There are presently several techniques for performing this task, including AC electric corona arcing, direct heating, and plasma etching. These methods have not been completely satisfactory when applied to the biologically compatible dielectric materials which must be used for implants, either because they fail to leave a cleanly and accurately exposed electrode surface, or because the dielectric material forming the rim of the electrode does not adhere satisfactorily and tightly to the wire surface. Mechanical removal of the insulation is very time-consuming and has a high probability of damaging the wire.

Additionally, multiple conductor micro-electrode arrays have been produced using photolithographic-integrated circuit production techniques. These arrays, however, are too delicate for this application. Additionally, such microelectrode arrays lack conductors for connection to other electrical circuitry. The attachment of conductors to such devices, moreover, typically creates a potential failure point.

Techniques that do not involve the accurate removal of insulating dielectric material have also been used to create electrodes for use in a cochlear implant. These techniques are, however, more time and labor intensive than the techniques taught here. Furthermore, it would be virtually impossible to attempt to create an implant with the density of electrodes taught herein using the prior techniques.

Use of red light ruby lasers to pierce dielectric coatings in preparation of microelectrodes was described by M. J. Mela in 1965 in an article entitled "Microperforation with Laser Beam in the Preparation of Microelectrodes," published in *IEEE Transactions on Biomedical Engineering*, Vol. BME-13, No. 2, pp. 70–76. Unfortunately the use of this type of laser leaves remnants of dielectric coating on the metal surface of the electrode. These remnants interfere with the electrode's ability to emit electrical current. That is, before the present invention it has not been known how to remove biologically compatible dielectric materials cleanly from a metal surface using a laser to produce well-defined, efficient electrodes.

In addition, the helical shape of the cochlea makes it very difficult to place an implant so that it reaches the most remote portion of the scala tympani. Ideally the implant should extend to within 5 mm of the distal terminus of the 25 mm long scala tympani. The preferred location is at the modiolar wall of the scala tympani, which is adjacent to the auditory nerve cells. Pre-shaped cores, shaped insulators with extensions to force the implant to the inner wall, and spiralled implants have all been tried.

The complexity of the shape of the scala tympani, however, a helical structure that turns more tightly at the top and tapers inward, presents a very difficult challenge not yet sufficiently answered. Complicating the problem is the possibility of damage either to the scala tympani or the implant during the insertion process. The techniques heretofore used have generally not proven adequate to allow the safe yet deep insertion of an implant.

SUMMARY OF THE INVENTION

An object of the present invention is, therefore, to provide a novel multi-electrode cochlear implant.

Another object of the present invention is to provide a multi-electrode cochlear implant that may be economically produced.

A further object of the present invention is to provide a multi-electrode cochlear implant that includes electrodes with an improved capability for emitting current.

Yet another object of the present invention is to provide a multi-electrode cochlear implant having electrodes formed and placed with great precision and accuracy.

Still another object of the present invention is to provide a multi-electrode cochlear implant that may be inserted into more complete and beneficial contact with the cochlea than was heretofore generally achievable.

Still another object of the present invention is to provide a high density multi-electrode cochlear implant in which the electrodes are configured not only longitudinally along the length of the implant but are also arranged laterally at separate locations along the circumference of the implant.

The present invention is a multi-electrode cochlear implant comprising a plurality of fine wires electrically insulated from one another and held together about a flexible insulating tube by a quantity of a dielectric material. Each electrode comprises a small area of a particular wire where the dielectric materials have been removed by a laser beam. The laser beam also seals the dielectric material to the wire by heating around the periphery of the electrode. The laser beam may also be controlled to heat the metal surface to the point where it is roughened, thereby increasing the surface area and the current emitting capability of the electrode. To further increase the current emitting capability of the electrode, a further layer of conductive metal, such as platinum black, may be deposited and electrically connected with the electrode in such a manner that its surface is particularly rough.

A core of shape memory material, such as nickel-titanium alloy, comprised of substantially 50% nickel and 50% titanium, may be placed inside a portion of the flexible tube. Alternatively a shape memory polymer may be used. This type of material may be formed so that at above a particular temperature it assumes a particular shape. In this case the it is formed so that it will assume a shape that will keep it into contact with the interior or "modiolor" wall of the scala tympani at body temperature.

Alternatively, the insulating tube about which the wires are wrapped may provide a lumen through which instruments or a guide wire may be extended to aid in the implant insertion process. It would also be possible to have the tube filled largely with shape memory material, but to leave empty a large enough cross-sectional area to allow the insertion of a guide wire.

In one embodiment of the invention a second layer or valence of wires coaxially surrounds a first layer of wires. In this embodiment, the first layer of wires or valence protrudes beyond the terminus of the second layer of wires to provide a stepwise approximation of the tapering of the scala tympani. In like manner, additional wire layers may be included.

A considerable advantage of the production technique described herein is that it yields the ability to create an implant with electrodes that are laterally separated from each other. This yields an increased ability to control precisely the amplitude of nerve stimulation.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
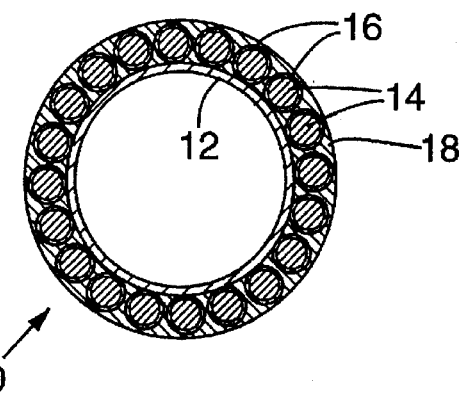
FIG. 1 is a greatly expanded cross-sectional view of a multi-electrode cochlear implant according to the present invention.
Figure 2:
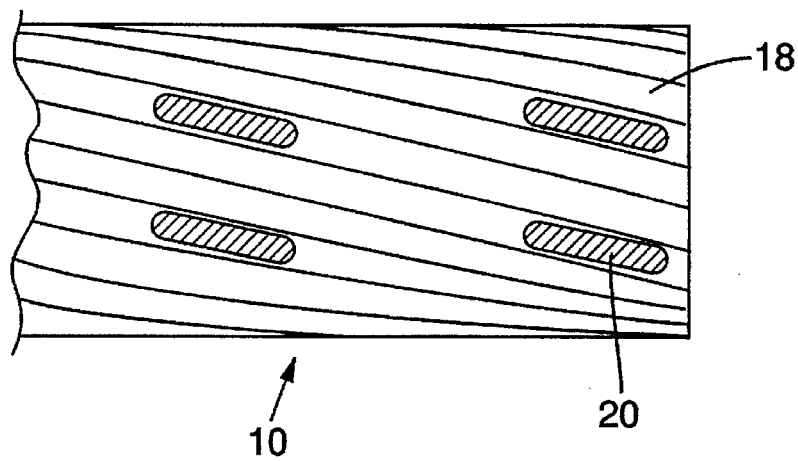
FIG. 2 is a greatly expanded side view of a portion of implant of FIG. 1, showing some electrodes.

A biologically implantable multi-electrode cochlear implant 10, shown in FIGS. 1–3, 7 and 8 is centered about a thin-walled tube 12. FIG. 9 describes the process of producing this cochlear implant. Several extremely fine wires 14, for example, twenty platinum or platinum alloy wires of American Wire Gauge 50, having a wire diameter of approximately 25 μm (0.001 inch), insulated from one another by suitable individual coatings 16 of flexible dielectric material are wrapped around the thin walled tube 12 in a helical serving in which the individual fine wires 14 lie neatly alongside one another without overlapping. This process is shown in block B10 of FIG. 9. A comprehensive coating 18 of dielectric material covers and binds together this structure. Dielectric materials which are usable for coating 18 must be biocompatible elastomers with good insulating properties such as silicone, a coating of which is available from PI Medical, 16125 S. W. 72 Avenue, Portland Oreg. 97224, under the trademark Silablate®. Also appropriate for this use are fluorocarbons, polyimides or derivatives thereof, epoxies, enamel, or a polymer of parachloroxylylene, such as that available from Union Carbide Corporation under the trademark Parylene-C®.

Comprehensive coating 18 is very thin and completely covers the implant, including the distal end. If Parylene-C® is used, for example, it may be vacuum deposited on the surface of wire coatings 16 and have a thickness of 6–12 μm. This process is shown in block B12 of FIG. 9.

An active electrode 20 of dimensions 20 by 100 μm is created by removing the coatings of dielectric material 16, 18 by exposing them to an ultraviolet laser beam focused with a lens to a 20 μm diameter spot and scanned over the desired 100 μm length. This process is shown in block B14 of FIG. 9.

A frequency-quadrupled YAG (FQY) laser operated in the fundamental transverse electromagnetic (TEM$_{00}$) mode is suitable to ablate portions of the coating 16, 18. Such a laser has a 266 nanometer wavelength which is in the ultraviolet (UV) range. Typically, this laser is Q-switched at around 1–20 KHz, producing a 40 ns full-width half maximum (FWHM) pulse, producing a fluence of approximately 10–50 joules/cm$^2$, at an average power of 300–400 milliwatts.

It has been found that such a highly focused laser beam in the ultraviolet frequency band is readily absorbed by dielectric coatings 16, 18 and is absorbed by the surfaces of wires 14, which are typically made of platinum or a platinum alloy, with the result that coatings 16, 18 are both photoablated by the laser beam and vaporized through contact with the heated metal which quickly reaches temperatures exceeding 1000° C. This process removes coatings 16, 18 cleanly from wire 14 surfaces.

The FQY laser beam spot can be moved under computer software control to scan coatings 16, 18 to remove them from the conductor body. Scanning control can be provided, for example, by equipment designed to control lasers for use in manufacture of integrated circuit products, such as is available from Electro Scientific Industries, Inc., of Beaverton, Oreg. Preferably, the UV laser is utilized together with exhaust and positive gas pressure systems to keep debris away from the focusing lens and the area where dielectric material is being ablated. Operation of the laser at the powers mentioned above provides an effective range of etch depths of approximately 1–50 microns in silicone, polyamide or Parylene-C® (polypara-chloroxylylene).

Coatings 16, 18 rimming the active electrodes are also heated by the effects of the UV laser beam. As a result, this portion of coatings 16, 18 melts, fuses together, solidifies and forms a strong adhesive bond with underlying wire 14. This bond hermetically seals the rest of the wire 14 from electrode 20 opening and serves to, among other valuable functions, reduce cross-talk among wires 14.

The spacing and orientation of the active electrodes 20 corresponding to the several fine wires 14 may be chosen as desired consistent with the pitch of the helical wrapping of fine wires 14 about the core. When desired, active electrode 20 may be spaced radially about implant 10, or they may be spaced longitudinally in a helical arrangement along the implant 10, separated more or less from one another as determined by the number of adjacent ones of the fine wires 14 which are skipped between consecutive active contact sites 20 defined along the implant 10.

Figure 3:
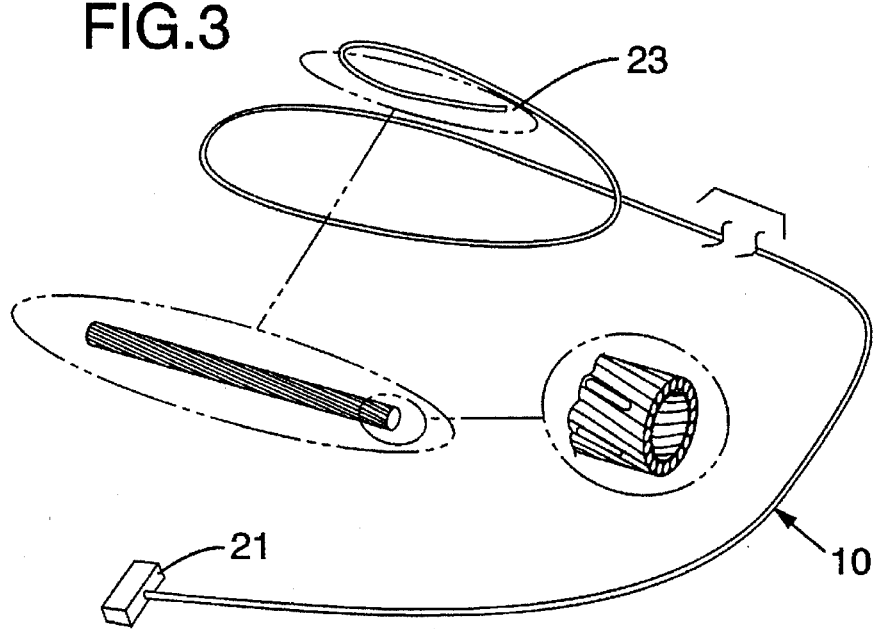
FIG. 3 is an expanded perspective view of the implant of FIG. 1 configured in the shape of the scala tympani.

FIG. 3 shows a cochlear implant configured in the shape of the scala tympani. The proximal end 21 of the implant 10 is equipped with a connector. The distal end 23 of the implant is adhered together with the comprehensive dielectric material 18.

Figure 4:
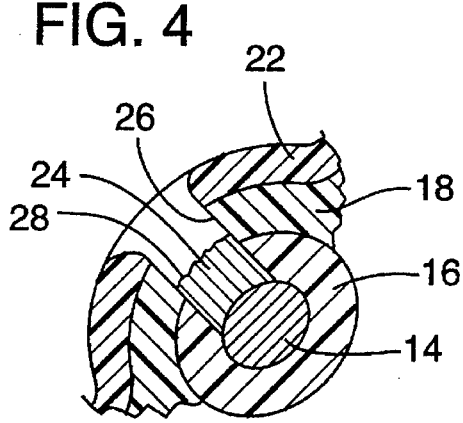
FIG. 4 is a greatly expanded cross-sectional view of an electrode of the multi-electrode cochlear implant of the present invention.

Further metal may be electrophoretically deposited into the electrodes 20. FIG. 4 shows an electrode 20 of the preferred embodiment of the present invention. An optional third layer 22 of dielectric material has been added here for further protection. More significantly, platinum black 24 has been electrophoretically deposited on wire 14 surface in electrode opening 26. The rough surface 28 of this material serves to increase the surface area and therefore reduce resistance of the electrode 20 to the emission of electrical current.

Another potential coating for an electrode 20 surface is comprised of iridium with a surface layer of iridium oxide. Alternatively iridium alone can be applied. Iridium is conductive and the surface layer of iridium oxide provides a large current releasing capacity. One method of producing such a coating can be initiated after the application of the second dielectric material 18. At this point, a layer of water soluble "resist" material, familiar to skilled persons in the art of integrated circuit fabrication, is applied to the implant. Next, the electrodes are formed by application of the laser beams, which removes the "resist" material as well as the dielectric coatings 16, 18. The implant is then placed in a chamber and sputtered with iridium. A surface layer of iridium oxide may also be sputtered on at this point. After removing the underlying resist material layer by submerging the implant in a dissolving solution, the only iridium remaining on the implant is that on the electrodes 20.

As an alternative to sputtering, cyclic voltametry can be used for creating the layer of iridium oxide on the iridium coating. In this method, the implant, after the steps of creating electrodes with a laser beam, is submerged in a bath of electrolytes and subjected to a voltage that causes the iridium to oxidize rapidly.

Figure 5:
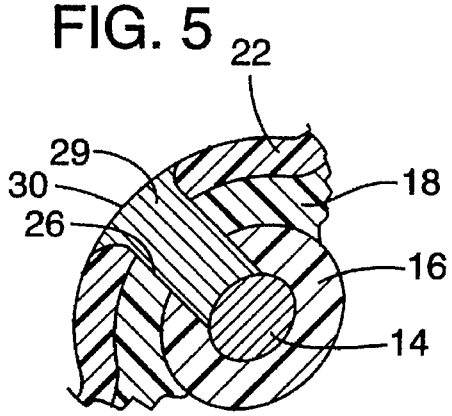
FIG. 5 is a greatly expanded cross-sectional view of an electrode of an alternative embodiment of the multi-electrode cochlear implant of the present invention.
Figure 6:
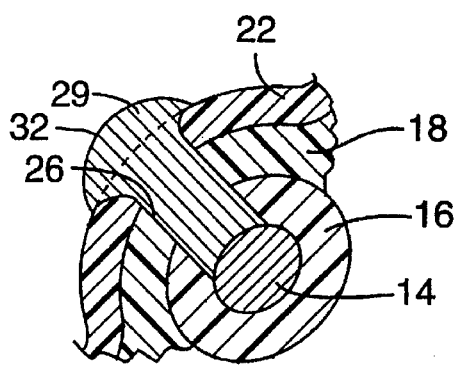
FIG. 6 is a greatly expanded cross-sectional view of an electrode of another alternative embodiment of the multi-electrode cochlear implant of the present invention.

FIGS. 5 and 6 show the electrode opening 26 electrophoretically filled to an even surface 30 (FIG. 5) or overfilled to a bulging surface 32 (FIG. 6) with either platinum or iridium 29.

Figure 7:
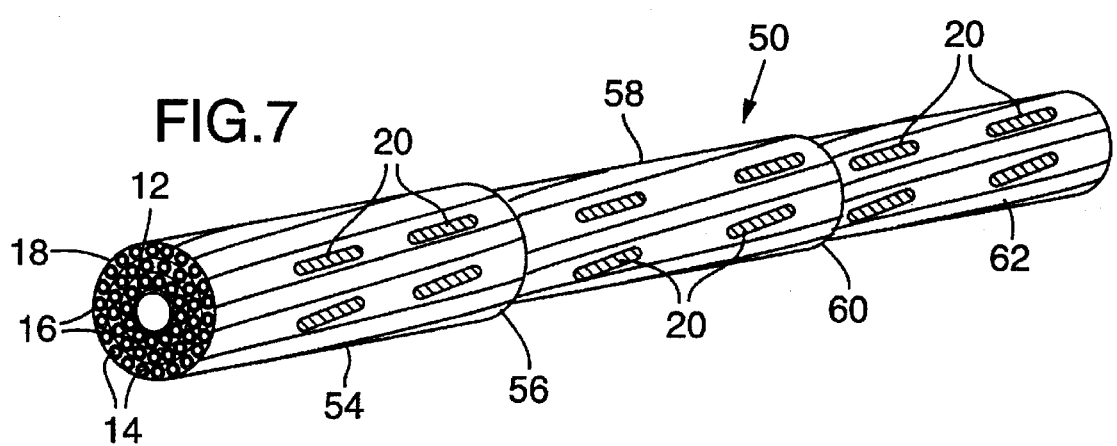
FIG. 7 is a greatly expanded perspective view of an alternative embodiment of the present invention.

FIG. 7 is a greatly expanded perspective view of an alternative embodiment of a cochlear implant 50 in which the thickness of implant 50 follows a stepwise approximation to a proportion of the width of the scala tympani. In this embodiment three layers or valences of wires are coaxially wound around each other. The outermost valence 54 includes a set of four electrodes 20 located slightly proximally of the distal termination 56 of valence 54. Typically the electrodes 20 are spaced approximately 300 μm apart longitudinally.

Note that for every longitudinal position of the electrodes 20 there are two electrodes 20 spaced apart laterally by about an eighth of a circumference (@ 100 μm). The lateral placement of electrodes serves the important function of allowing the lateral positioning and orientation of the potential gradients. This in turn permits a more precise control of the potential gradients.

In the interior of valence 54 resides a second valence 58. Second valence 58 continues in the distal dimension past the distal terminus 56 of outermost valence 54. All of the electrodes 20 of second valence 58 are located in this portion. The innermost valence 62 protrudes approximately 1 cm past the distal terminus 60 of second valence 58. The electrodes 20 of innermost valence 62 are located in this protrusion. Not only are more wires and therefore more electrodes 20 possible in this embodiment but the gradual stepwise narrowing of the implant mirrors the narrowing of the cochlea.

The distal section of the preferred embodiment includes a core made of a shape memory material, such as nickel-titanium alloy made of substantially 50% nickel and 50% titanium. This material has the unusual property that it may be prepared in such a manner that it will, upon reaching some predetermined temperature, assume a predetermined shape. In this case the nitinol would be treated to assume the shape of the scala tympani when it is heated to body temperature or above. At below human body temperature the shape memory material would be quite malleable and flexible, allowing it to be inserted a preliminary distance. As it is inserted further, warming up in the process, it will begin to curve allowing for easier insertion through the curves of the scala tympani. Finally, when it is completely installed and warmed to body temperature, it will assume the shape of the scala tympani but in a form tight enough so that it will contact the interior modiolar wall where the auditory neurons have their receptive terminus.

Figure 8:
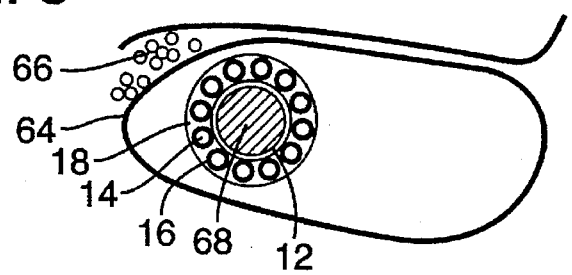
FIG. 8 is a greatly expanded cross-sectional view of the implant of FIG. 1 inside the scala tympani.
Figure 9:
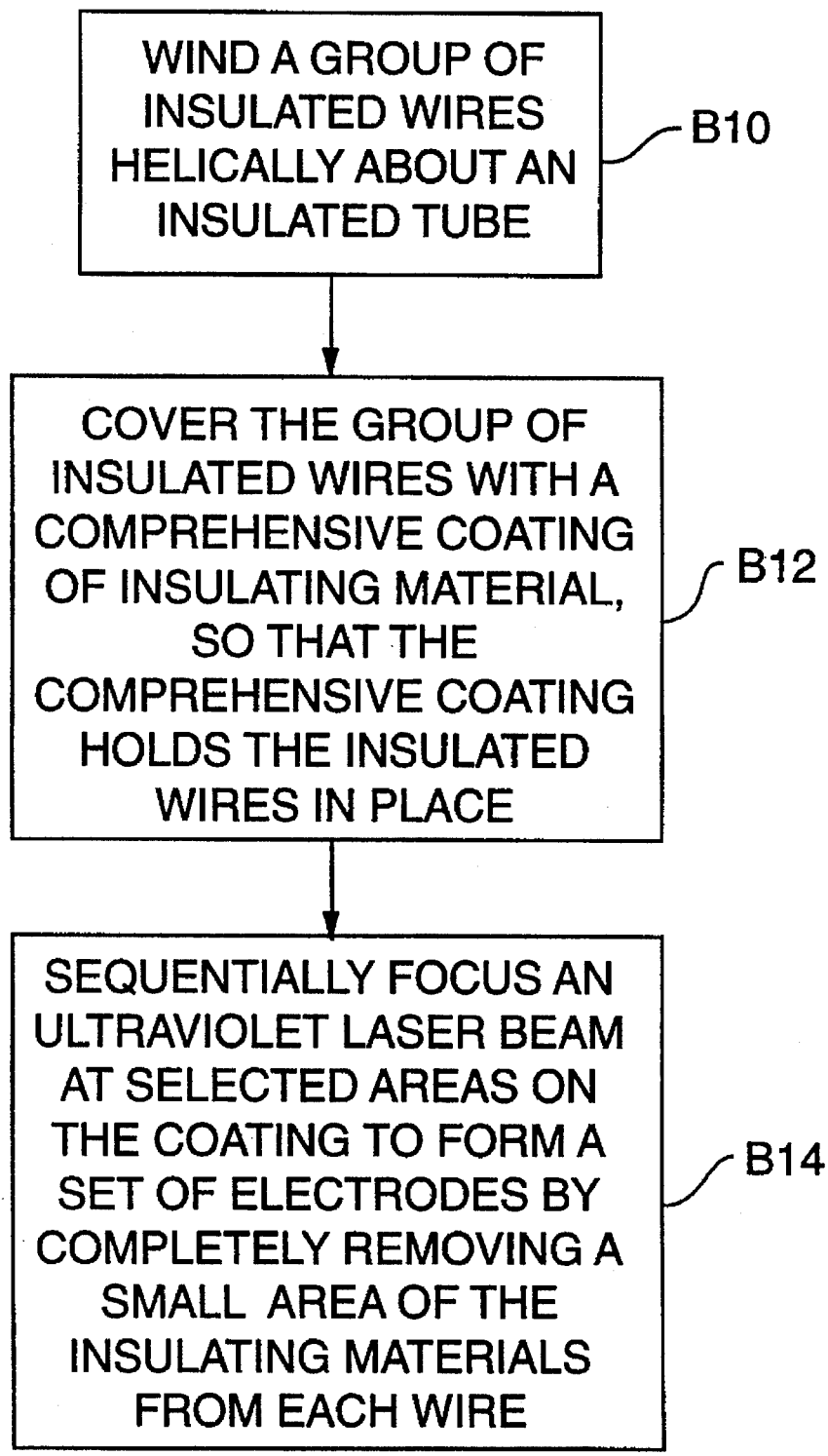
FIG. 9 is a flow diagram showing a method of producing a cochlear implant according to the present invention.

FIG. 8 is a greatly expanded cross-sectional view of the implant in the scala tympani. In this depiction the implant is held close to the modiolar wall 64 and the nearby nerve cells 66 by the shape memory core 68.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A multi-electrode cochlear implant, comprising:
    a flexible core;
    a plurality of fine wires, each having a wire surface collectively helically disposed about said tube;
    a plurality of dielectric material coatings, each coating disposed about a unique one of said wires;
    a quantity of a second dielectric material having an outer surface and disposed about said plurality of fine wires and holding said plurality of fine wires together about said core;
    a first opening extending inwardly from said outer surface, through said first and second dielectric material, to a portion of a first one of said wire surfaces, thereby forming a first electrode; and
    a second opening extending inwardly from said outer surface, through said first and second dielectric material, to a portion of a second one of said wire surfaces, thereby forming a second electrode.

2. The cochlear implant of claim 1 wherein each said opening is partially filled with a layer of material comprised of a metal.

3. The cochlear implant of claim 2 wherein said material is platinum black.

4. The cochlear implant of claim 2 wherein said material is iridium.

5. The cochlear implant of claim 2 wherein said material is iridium oxide.

6. The cochlear implant of claim 2 wherein said material is iridium and said openings further comprise a surface layer of iridium oxide deposited on top of said iridium.

7. The cochlear implant of claim 1 wherein said wires are comprised of platinum.

8. The cochlear implant of claim 1 wherein said wires are comprised of a platinum alloy.

9. The cochlear implant of claim 1 wherein said wires are comprised of gold.

10. The cochlear implant of claim 1 wherein said wires are comprised of a gold alloy.

11. The cochlear implant of claim 1 wherein said second dielectric material is biocompatible.

12. The cochlear implant of claim 1 wherein said second dielectric material is comprised of silicone.

13. The cochlear implant of claim 1 wherein said core is comprised of shape memory material, said core forming itself into the shape of the human cochlea at human body temperature.

14. The cochlear implant of claim 13 wherein said shape memory material is an alloy comprised of substantially 50% titanium and 50% nickel.

15. The cochlear implant of claim 13 wherein said shape memory material is a polymer.

16. The cochlear implant of claim 1 further having a longitudinal or lengthwise dimension and a lateral dimension perpendicular to said longitudinal dimension and wherein said first electrode is spaced slightly laterally apart from said second electrode.

17. The cochlear implant of claim 1 wherein said core comprises a tube having an interior space, said interior space being available for the accommodation of a guide wire during the implant insertion process.

18. A multi-electrode cochlear implant having a proximal and a distal end, comprising:
    a flexible core;
    a first valence comprised of a multiplicity of first fine wires, each wire having a surface and being disposed about said core and a multiplicity of dielectric material coatings, each disposed about one of said fine wires, said first valence having a distal end;
    a second valence comprised of a multiplicity of second fine wires, each having a surface and being disposed about said first valence and a multiplicity of second dielectric coatings, each disposed about a single one of said second fine wires, said second valence having a distal end that is proximal to the distal end of said first valence;
    a quantity of a second dielectric material having an outer surface and disposed about said first and second valence and holding said first and second wires in place;
    a first opening in said first valence extending inwardly from said outer surface through said first and second dielectric material to a first one of said wire surfaces and thereby forming an electrode;
    a second opening in said first valence extending inwardly from said outer surface through said first and second dielectric material to a second one of said wire surfaces and thereby forming a second electrode;
    a first opening in said second valence extending inwardly from said outer surface through said first and second dielectric material to a first one of said second wire surfaces and thereby forming a third electrode; and
    a second opening in said second valence extending inwardly from said outer surface through said first and second dielectric material to a second one of said wire surfaces and thereby forming a fourth electrode.

19. The implant of claim 18 wherein said core is comprised of shape memory material.

20. A method of producing a cochlear implant, comprising:
    winding a group of insulated wires helically about a flexible tube;
    covering said group of insulated wires with a comprehensive coating of insulating material, said additional coating holding said wires in place; and
    sequentially focusing an ultraviolet laser beam at selected areas on said coating to form a set of electrodes by completely removing a small area of said insulating materials from each said wire.

21. The method of claim 20 further including the step of electrophoretically depositing a layer of platinum black onto said electrodes.

22. The method of claim 20 further including the step of depositing by sputtering a material comprised of iridium onto said electrodes.

23. The method of claim 22 further including the step of producing a surface layer of iridium oxide on said material by the process of cyclic voltametry wherein said electrodes are submerged in a bath of electrolytes and subjected to a voltage sufficient to cause the iridium to oxidize.

24. The method of claim 20 wherein said core comprised of shape memory material having the property of assuming the shape of the scala tympani at temperatures above 35° C. (95° F.).

25. The method of claim 24 wherein said shape memory material is comprised substantially of 50% nickel and 50% titanium.

26. The method of claim 24 wherein said shape memory material is a shape memory polymer.

27. A multi-electrode implant, comprising:

a flexible core;

a plurality of fine wires, each having a wire surface and being disposed about said tube;

a plurality of dielectric material coatings, each coating disposed about one of said wires;

a quantity of a second dielectric material having an outer surface and disposed about said plurality of fine wires and holding said plurality of fine wires together about said tube;

a first opening extending inwardly from said outer surface, through said first and second dielectric material, to a portion of a first one of said wire surfaces, thereby forming a first electrode; and a second opening extending inwardly from said outer surface, through said first and second dielectric material, to a portion of a second one of said wire surfaces, thereby forming a second electrode.

* * * * *